United States Patent
Chalker, II et al.

(10) Patent No.: US 6,535,277 B2
(45) Date of Patent: Mar. 18, 2003

(54) METHODS AND APPARATUS FOR NON-INVASIVELY IDENTIFYING CONDITIONS OF EGGS VIA MULTI-WAVELENGTH SPECTRAL COMPARISON

(75) Inventors: B. Alan Chalker, II, Durham, NC (US); James E. Hutchins, Durham, NC (US)

(73) Assignee: Embrex, Inc., Research Triangle Park, NC (US)

( * ) Notice: Subject to any disclaimer, the term of this patent is extended or adjusted under 35 U.S.C. 154(b) by 234 days.

(21) Appl. No.: 09/742,167

(22) Filed: Dec. 20, 2000

(65) Prior Publication Data

US 2002/0075476 A1 Jun. 20, 2002

(51) Int. Cl.⁷ .................. A01K 43/00; G01N 33/08
(52) U.S. Cl. ........................... 356/53; 356/52
(58) Field of Search ...................... 356/52, 53, 54, 356/64, 66

(56) References Cited

U.S. PATENT DOCUMENTS

| | | |
|---|---|---|
| 1,816,483 A | 7/1931 | Heaton |
| 2,175,262 A | 10/1939 | Haugh |
| 2,321,900 A | 6/1943 | Dooley .................. 88/14.1 |
| 2,520,610 A | 8/1950 | Powell |
| 2,823,800 A | 2/1958 | Bliss .................... 209/111 |
| 2,849,913 A | 9/1958 | Bohlman |
| 3,060,794 A | 10/1962 | Reading |
| 3,241,433 A | 3/1966 | Niederer et al. |
| 3,255,660 A | 6/1966 | Hirt |
| 3,616,262 A | 10/1971 | Broomall et al. |
| 3,740,144 A * | 6/1973 | Walker .................... 356/53 |
| 4,039,259 A * | 8/1977 | Saito et al. ................ 356/53 |
| 4,182,571 A | 1/1980 | Furuta et al. ............. 356/53 |
| 4,458,630 A | 7/1984 | Sharma et al. |
| 4,671,652 A | 6/1987 | Van Asselt et al. |
| 4,681,063 A | 7/1987 | Hebrank |
| 4,914,672 A | 4/1990 | Hebrank |
| 4,955,728 A | 9/1990 | Hebrank |
| 5,017,003 A | 5/1991 | Keromnes et al. |
| 5,028,421 A | 7/1991 | Fredericksen et al. |
| 5,158,038 A | 10/1992 | Sheeks et al. |
| 5,615,777 A * | 4/1997 | Weichman et al. ......... 209/511 |
| 5,745,228 A | 4/1998 | Hebrank et al. |
| 5,900,929 A | 5/1999 | Hebrank et al. .............. 356/52 |

FOREIGN PATENT DOCUMENTS

| | | |
|---|---|---|
| DE | 39 04675 | 8/1990 |
| EP | 1074831 A1 | 2/2001 |
| GB | 1112823 | 5/1968 |
| JP | 60079249 | 7/1985 |

* cited by examiner

Primary Examiner—Frank G. Font
Assistant Examiner—Roy M Punnoose
(74) Attorney, Agent, or Firm—Myers Bigel Sibley & Sajovec (57) ABSTRACT

Methods and apparatus that can non-invasively identify the present condition of eggs, namely, whether an egg is a live egg, a clear egg, an early dead egg, a middle dead egg, a late dead egg, a rotted egg, a cracked egg, and/or an inverted egg, are provided. An egg is illuminated with both visible and invisible light at wavelengths of between about three hundred nanometers and about eleven hundred nanometers (300 nm–1,100 nm). Light passing through the egg is received at a detector positioned such that a path of the received light does not pass through an aircell within the egg, except in the case of an inverted egg. The intensity of the light is determined at a plurality of the visible and infrared wavelengths, and a spectrum that represents light intensity at selected ones of the visible and infrared wavelengths is generated. The generated spectrum is compared with one or more spectra associated with a respective known egg condition to identify a present condition of the egg.

36 Claims, 7 Drawing Sheets

METHODS AND APPARATUS FOR NON-INVASIVELY IDENTIFYING CONDITIONS OF EGGS VIA MULTI-WAVELENGTH SPECTRAL COMPARISON

FIELD OF THE INVENTION

The present invention relates generally to eggs and, more particularly, to methods and apparatus for classifying eggs.

BACKGROUND OF THE INVENTION

Discrimination between poultry eggs on the basis of some observable quality is a well-known and long-used practice in the poultry industry. "Candling" is a common name for one such technique, a term which has its roots in the original practice of inspecting an egg using the light from a candle. As is known to those familiar with poultry eggs, although egg shells appear opaque under most lighting conditions, they are in reality somewhat translucent, and when placed in front of a direct light, the contents of the egg can be observed.

In most practices, the purpose of inspecting eggs, particularly "table eggs" for human consumption, is to identify and then segregate those eggs which have a significant quantity of blood present, such eggs themselves sometimes being referred to as "bloods" or "blood eggs." These eggs are less than desirable from a consumer standpoint, making removal of them from any given group of eggs economically desirable.

Eggs which are to be hatched to live poultry also may be candled midway through embryonic development or later to identify infertile ("clear") eggs and remove them from incubation to thereby increase available incubator space. Such inspection and removal is particularly useful in turkey hatcheries. Candlers also attempt to identify and remove "rotted" and other dead eggs on the basis of their internal color. Unfortunately, conventional techniques may be difficult and unreliable, however, so that dead and rotted eggs may be inadvertently returned to incubation.

U.S. Pat. Nos. 4,955,728 and 4,914,672, both to Hebrank, describe a candling apparatus that uses infrared detectors and the infrared radiation emitted from an egg to distinguish live from infertile eggs.

U.S. Pat. No. 4,671,652 to van Asselt et al. describes a candling apparatus in which a plurality of light sources and corresponding light detectors are mounted in an array, and the eggs passed on a flat between the light sources and the light detectors.

In recent years, spectrographic techniques have been developed which irradiate eggs with particular frequencies of light which are sensitive to the presence of one or more of the characteristic components of blood (e.g., hemoglobin) to make a more accurate determination of whether or not the contents of the egg are indeed filled with blood or whether some other factor is interfering with the egg's appearance or quality.

Other conventional techniques are used to inspect table eggs for the purpose of determining whether or not they are cracked. These techniques also use light sources and detectors because cracked eggs will often transmit more incident light towards a detector than will intact ones.

Recently, however, there have developed other reasons for distinguishing between eggs. One of these reasons is the advancements in techniques for treating poultry embryos with medications, nutrients, hormones or other beneficial substances while the embryos are still in the egg. Such techniques are quite advantageous compared to treatment of newly born chicks which often must be medicated, for example, by being hand inoculated one by one.

Injections of various substances into avian eggs are employed in the commercial poultry industry to decrease post-hatch mortality rates or increase the growth rates of the hatched bird. Similarly, the injection of virus into live eggs is utilized to propagate virus for use in vaccines. Examples of substances that have been used for, or proposed for, in ovo injection include vaccines, antibiotics and vitamins.

Examples of in ovo treatment substances and methods of in ovo injection are described in U.S. Pat. No. 4,458,630 to Sharma et al. and U.S. Pat. No. 5,028,421 to Fredericksen et al., the contents of which are incorporated by reference herein in their entireties. The selection of both the site and time of injection treatment can also impact the effectiveness of the injected substance, as well as the mortality rate of the injected eggs or treated embryos. See, e.g., U.S. Pat. No. 4,458,630 to Sharma et al., U.S. Pat. No. 4,681,063 to Hebrank, and U.S. Pat. No. 5,158,038 to Sheeks et al. U.S. Patents cited herein are hereby incorporated by reference herein in their entireties.

U.S. Pat. No. 3,616,262 to Coady et al. discloses a conveying apparatus for eggs that includes a candling station and an inoculation station. At the candling station, light is projected through the eggs and assessed by a human operator, who marks any eggs considered non-viable. Non-viable eggs are manually removed before the eggs are conveyed to the inoculating station.

Figure 1A:
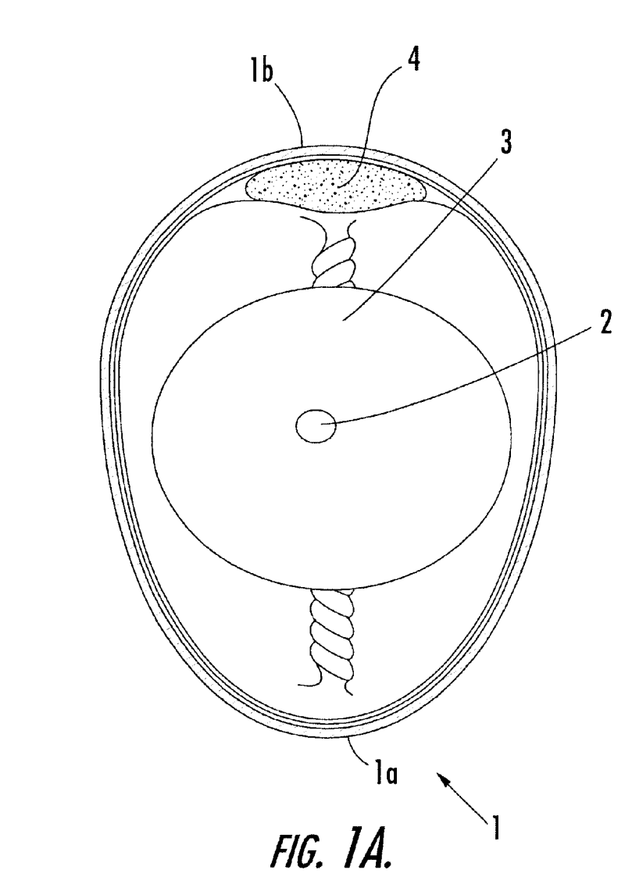
FIG. 1A illustrates a live chicken egg at day one of incubation.
Figure 1B:
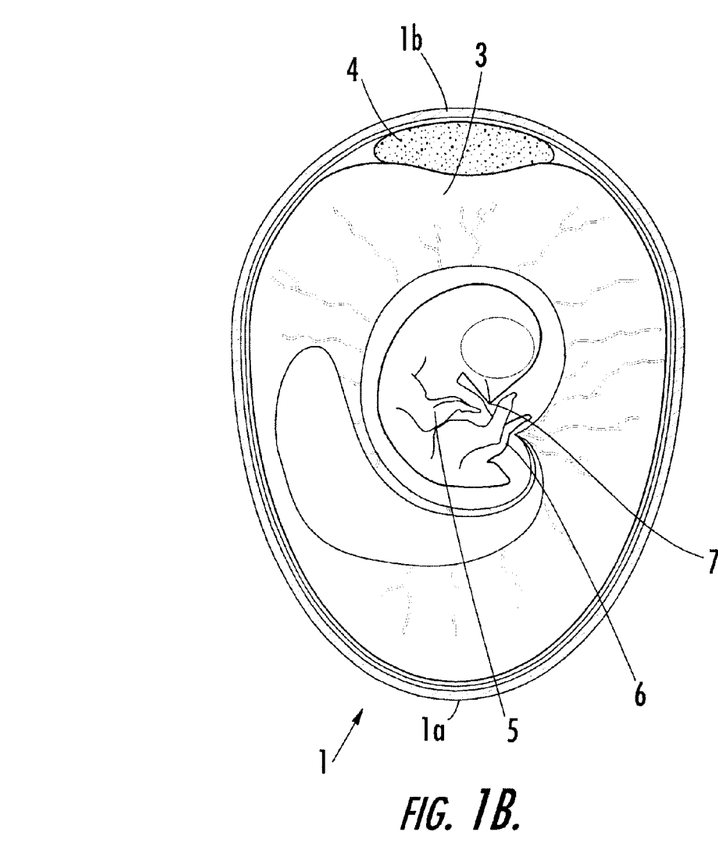
FIG. 1B illustrates a live chicken egg at day twelve of incubation.

Poultry eggs (hereinafter "eggs") are typically inoculated on or about the eighteenth day of incubation. At such time, an egg may be one of several commonly recognized types. An egg may be a "live" egg, meaning that it has a viable embryo. FIG. 1A illustrates a live egg 1 at day one of incubation. FIG. 1B illustrates a live egg 1 at day twelve of incubation. The egg 1 has a somewhat narrow end in the vicinity represented at 1a as well as an oppositely disposed broadened end portion in the vicinity shown at 1b. In FIG. 1A, an embryo 2 is represented atop the yolk 3. The egg 1 contains an air cell 4 adjacent the broadened end 1b. As illustrated in FIG. 1B, the wings 5, legs 6, and beak 7 of a baby chick have developed.

An egg may be a "clear" or "infertile" egg, meaning that it does not have an embryo. More particularly, a "clear" egg is an infertile egg that has not rotted. An egg may be an "early dead" egg, meaning that it has an embryo which died at about one to five days old. An egg may be a "mid-dead" egg, meaning that it has an embryo which died at about five to fifteen days old. An egg may be a "late-dead" egg, meaning that it has an embryo which died at about fifteen to eighteen days old.

An egg may be a "rotted" egg, meaning that the egg includes a rotted infertile yolk (for example, as a result of a crack in the egg's shell) or, alternatively, a rotted, dead embryo. While an "early dead", "mid-dead" or "late-dead egg" may be a rotted egg, those terms as used herein refer to such eggs which have not rotted. Clear, early-dead, mid-dead, late-dead, and rotted eggs may also be categorized as "non-live" eggs because they do not include a living embryo.

An egg may be an "empty" egg, meaning that a substantial portion of the egg contents are missing, for example, where the egg shell has cracked and the egg material has leaked from the egg. Additionally, from the perspective of many egg detecting and identifying devices, an egg flat may be missing an egg at a particular location, in which case, this location may be termed a "missing" egg. An egg may be placed in an egg flat such that it is an "upside-down" or "inverted" egg, meaning that the egg has been placed in the flat such that the air cell thereof is mislocated, typically with the blunt end down.

Typically, eggs are held in flats on racks in carts for incubation in relatively large incubators. At a selected time, typically on the eighteenth day of age, a cart of eggs is removed from the incubator for the purposes of, ideally, separating out unfit eggs (namely, dead eggs, rotted eggs, empties, and clear eggs), inoculating the live eggs and transferring the eggs from the setting flats to the hatching baskets. Certain practical aspects of the incubation, handling and measuring processes may substantially diminish the accuracy of the methods and apparatus for distinguishing between live and dead eggs using conventional techniques.

While it is disadvantageous to discard live eggs, it is also disadvantageous to retain certain non-live eggs. In particular, if rotted or dead eggs are retained and inoculated, the inoculating needle may be contaminated, risking infection of subsequent live, healthy eggs. Furthermore, a treatment substance is wasted if injected in a non-live egg.

Furthermore, in some instances, it may be desirable to identify clear eggs (i.e., infertile, non-rotted eggs) and early dead eggs. While not suitable for producing broilers, these eggs may be useful for commercial food service or low grade food stock (e.g., dog food). The presence of bacterial contamination from rots decreases the value of this food stock.

In hatchery management, it is desirable to acquire information about the various types of eggs in each set of eggs. For example, it is desirable to know how many dead eggs are in a particular set of eggs. This information can be valuable because changes in the relative percentage of the various types of eggs are known to be caused by specific factors, such as improper incubator temperature settings, improper humidity, age and health of the flock of hens that laid the eggs, and the like. Unfortunately, current techniques for obtaining this information typically require destroying several hundred eggs from each set.

Although conventional tests for appearance and blood can discriminate to some extent between fertile and infertile eggs, there may be no reliable, automatic methods for distinguishing between live and dead eggs. Conventional candling techniques cannot effectively distinguish rotted eggs or late dead eggs from live eggs. Moreover, conventional candling techniques are generally unable to classify dead eggs as early dead, middle dead, or late dead. Therefore, there is a need for a highly reliable method of determining the condition of eggs, i.e., classifying eggs as live, dead (early, mid and late), clear, and/or rotted.

SUMMARY OF THE INVENTION

In view of the above discussion, embodiments of the present invention provide methods and apparatus that can non-invasively identify the present condition of eggs, namely, whether an egg is a live egg, a clear egg, an early dead egg, a middle dead egg, a late dead egg, a rotted egg, a cracked egg, and/or an inverted egg. According to embodiments of the present invention, a method of non-invasively identifying the present condition of eggs includes illuminating an egg with both visible and invisible light at wavelengths of between about three hundred nanometers and about eleven hundred nanometers (300 nm–1,100 nm). Light passing through an egg is received at a detector positioned such that a path of the received light does not pass through an aircell within the egg, except in the case of an inverted egg.

Preferably, a light source is positioned adjacent the end of an egg that is opposite the aircell, and a detector is positioned adjacent the egg at an angle of between about ten degrees and about ninety degrees (10°–90°) relative to a longitudinal axis of the egg. Moreover, the light source is preferably in contacting relationship with the egg such that light reflecting off of the egg shell is reduced. The light source does not necessarily need to be in contacting relationship with the egg. A collimated (i.e., focused) beam of light can also be utilized to reduce the amount of light reflected off of the egg shell.

The intensity of light passing through an egg is determined at a plurality of the visible and infrared wavelengths, and a spectrum that represents light intensity at selected ones of the visible and infrared wavelengths is generated. The generated spectrum then is compared with one or more spectra associated with a respective known egg condition to identify a present condition of the egg. For example, the generated spectrum may be compared with a respective spectrum associated with one or more of the following: live eggs, early dead eggs, middle dead eggs, late dead eggs, clear eggs, cracked eggs, rotted eggs, and/or inverted eggs.

According to embodiments of the present invention, an apparatus for processing eggs is provided that includes an identifier configured to determine a present condition of each of a plurality of eggs. The identifier includes a light source and a spectrometer. The light source illuminates each egg with light in both visible and infrared wavelengths between about three hundred nanometers and about eleven hundred nanometers (300 nm–1,100 nm). The spectrometer receives light passing through each egg and obtains intensity values of the received light at selected ones of the visible and infrared wavelengths. The spectrometer, or a processor in communication with the spectrometer, converts light intensity values for each egg into a respective spectrum and compares each generated spectrum with a plurality of spectra, wherein each of the spectra are associated with a respective known egg condition. A display may be provided that displays the identified present condition of each of the eggs.

According to additional embodiments of the present invention, an egg removal apparatus may be provided downstream from the identifier. The egg removal apparatus may be configured to remove eggs identified as live, dead, clear, cracked, rotted, or inverted. In addition, a plurality of injectors may be provided downstream from the identifier. Each injector may be configured to inject a substance into a respective egg identified as a live egg, and/or to remove material from a respective egg identified as a live egg.

The present invention may be advantageous because identification of live eggs versus non-live eggs (i.e., dead, rotted, cracked, clear, and inverted eggs) can be performed rapidly and more accurately than via conventional methods. Moreover, embodiments of the present invention are advantageous over conventional candling techniques which cannot effectively distinguish rotted eggs or late dead eggs from live eggs. As such, the number of improperly retained eggs (i.e., rotted and dead) which might otherwise contaminate inoculation needles can be reduced.

In addition, the possibility of discarding live eggs can be reduced. Accurate identification and removal of dead and rotted eggs may also provide a benefit during hatching of live eggs by removing a potential source of microbial contamination that could adversely affect chick health after hatch.

Identification methods and apparatus according to embodiments of the present invention may be used to further estimate the quantities or statistics of early dead, mid-dead, late-dead, rotted and empty eggs. Such information may be desired for the purposes of evaluating groups of eggs.

DETAILED DESCRIPTION OF THE INVENTION

The present invention now is described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Methods and apparatus according to embodiments of the present invention may be utilized for non-invasively identifying a present condition of an egg at any time during the embryonic development period (also referred to as the incubation period) thereof. Embodiments of the present invention are not limited to a particular day during the embryonic development period.

The term "classifying eggs" as used herein shall mean determining the present condition of eggs, i.e., whether an egg, at a given point in time, is fertile, live, dead (early, mid and late), clear, rotted, cracked, and/or inverted. In addition, embodiments of the present invention may be used to determine whether eggs contain certain substances. For example, the presence of substances to be harvested including, but not limited to, vaccines and recombinant protein products may be detected via embodiments of the present invention. Methods and apparatus according to embodiments of the present invention may be used to determine conditions of any types of avian eggs, including chicken, turkey, duck, geese, quail, and pheasant eggs.

Figure 2:
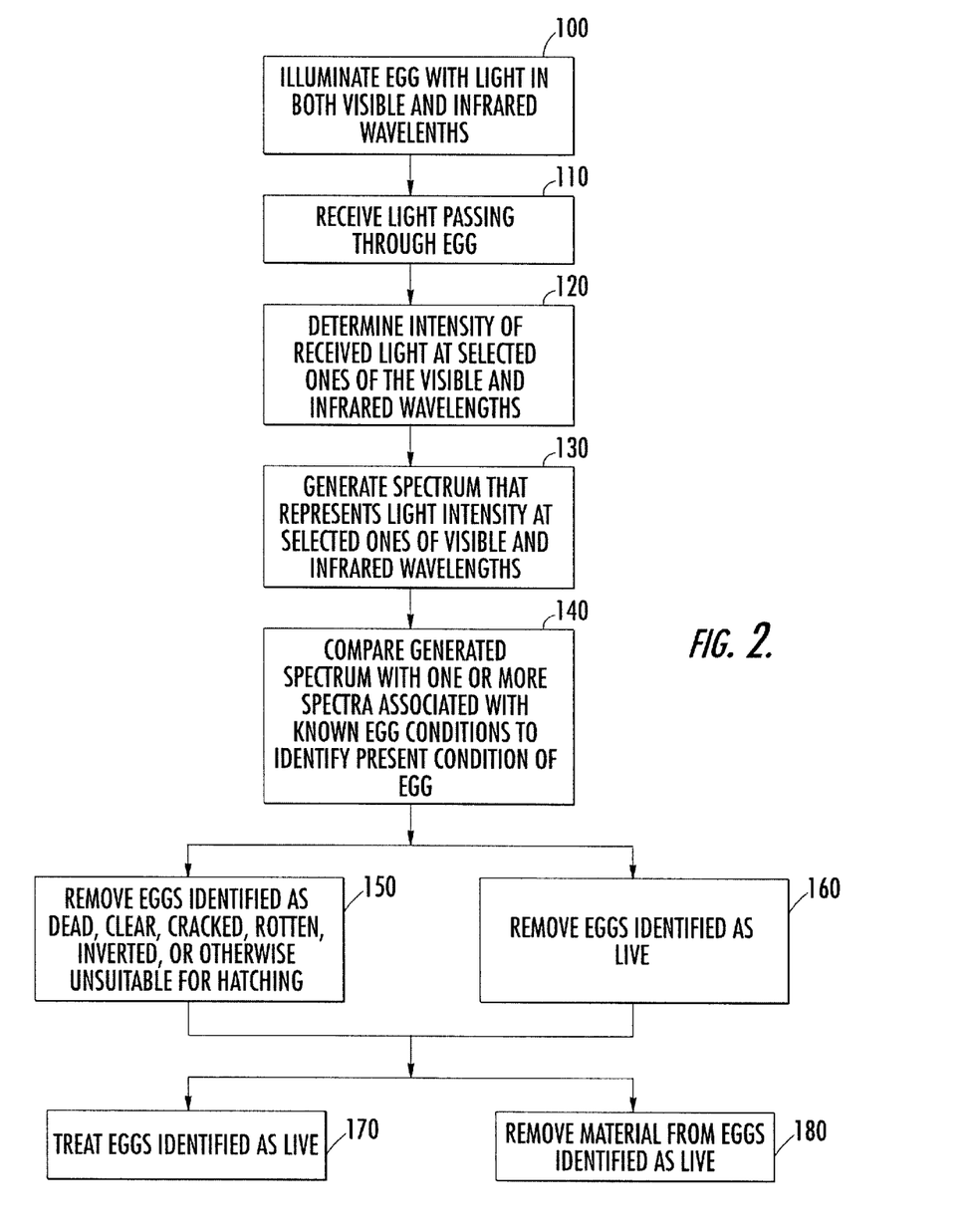
FIG. 2 is a flowchart of operations for noninvasively identifying a present condition of an egg via multi-wavelength spectral comparison, according to embodiments of the present invention.

Referring now to FIG. 2, a method of non-invasively identifying a present condition of an egg, according to embodiments of the present invention, is illustrated. An egg is illuminated with light in both visible and infrared wavelengths from a light source that is positioned adjacent an egg (preferably at or near the pointed or non-air cell end of an egg) (Block 100). As used herein, the term "pointed end" of an egg refers to the non-air cell end of an egg. The light source is preferably in contacting relationship with the egg, and/or a light beam from the light source is collimated, such that light scattering (i.e., light not entering the egg and reflecting off of the shell) is reduced.

A detector is positioned adjacent the egg and receives light passing through the egg (Block 110). Preferably, the detector is positioned such that a path of the received light from the light source does not pass through an aircell within the egg, except in the case of an inverted egg. Preferably, each egg is illuminated with light at wavelengths of between about three hundred nanometers and about eleven hundred nanometers (300 nm–1,100 nm).

The intensity of the received light is determined at selected ones of the visible and infrared wavelengths (Block 120). A spectrum that represents light intensity at selected ones of the plurality of visible and infrared wavelengths is generated (Block 130). A spectrum may be subjected to various processing algorithms that are based upon calibrated spectra. The generated spectrum is then compared with at least one spectrum, wherein each spectrum is associated with a respective known egg condition, to identify a present condition of the egg (Block 140). For example, the spectrum for an egg in question may be compared with a spectrum associated with the following types of eggs: fertile eggs, live eggs, early dead eggs, middle dead eggs, late dead eggs, clear eggs, cracked eggs, rotted eggs, inverted eggs, and/or eggs containing a specific substance. This comparison may involve processing a spectrum via an analytical model (consisting of one or more algorithms) which is built from known spectra. The outputs of an analytical model are designed to correspond with specific types of eggs.

Spectrum processing may involve adjusting a spectrum (either by selective scaling and/or shifting) based upon factors derived from calibration spectra obtained from reference eggs. This allows spectra produced by different detectors and at different times to be objectively compared. Additional processing of a spectrum before comparison with a reference spectrum may involve noise reduction (through techniques such as averaging multiple sequential spectra and/or "boxcaring", which involves averaging data points in a spectrum based upon nearest neighboring datapoints). Also, processing of a spectrum before comparison with a reference spectrum may involve feature extraction via techniques such as differentiation which extracts relative slopes of a curve, integration which extracts information about the area underneath a curve, and/or windowing which reduces a spectrum to specific information intensive ranges of wavelengths. Spectrum processing techniques such as those described herein are well understood by those of skill in the art and need not be described further herein.

An egg that is determined to be dead, clear, cracked, rotted, inverted, or otherwise unsuitable for hatching, may be removed, either automatically or by hand (Block 150). Removed eggs may be discarded or may be subjected to additional processing for various purposes. For example, clear and/or early dead eggs may be processed for use in dog food. Alternatively, an egg that is determined to be live may be removed from a flat containing non-live eggs (Block 160). An egg that is determined to be live may be injected with a treatment (or other) substance (Block 170), or material may be removed from a live egg (Block 180).

Figure 3A:
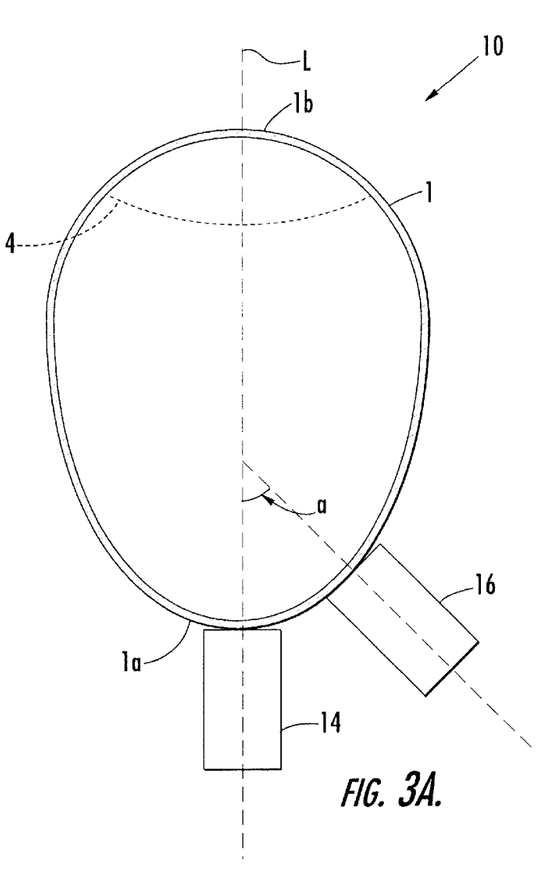
FIGS. 3A–3B illustrate identifiers for use in non-invasively identifying a present condition of an egg, according to embodiments of the present invention.

Referring now to FIG. 3A, an apparatus (referred to hereinafter as an "identifier") 10 for non-invasively identifying a present condition of an egg, according to embodiments of the present invention, is illustrated schematically. The illustrated identifier 10 includes a light source 14 that illuminates an egg 1 with light in both visible and infrared wavelengths, and a spectrometer 16 that receives light passing through the egg 1. The intensity of the received light is determined by the spectrometer 16 for selected ones of the visible and infrared wavelengths of light.

The spectrometer 16 preferably is configured (e.g., via a microprocessor) to convert light intensity values for an egg into a spectrum. In addition, the spectrometer 16 is configured to compare a generated spectrum for an egg with at least one spectrum associated with a known egg condition to identify a present condition of the egg. For example, a generated spectrum may be compared with a spectrum of an egg known to be live in order to determine whether the egg in question is a live egg. Similarly, comparisons with spectra associated with known conditions can be made to determine whether an egg in question is early dead, middle dead, late dead, clear, cracked, rotted, and/or inverted.

The light source 14 is configured to illuminate an egg with light at wavelengths of between about three hundred nanometers and about eleven hundred nanometers (300 nm–1,100 nm). Preferably, the light source 14 is configured to be positioned adjacent a pointed end 1a of an egg 1 (i.e., opposite the end of the egg containing the air cell 4), as illustrated. However, it is understood that the light source 14 can be offset from the pointed end. In addition, the spectrometer 16 is configured to be positioned adjacent the light source 14, preferably at an angle a of between about ten degrees and about ninety degrees (10°–90°) relative to a longitudinal axis L of the egg, wherein the pointed end of the egg defines zero degrees (0°) relative to the longitudinal axis L. By limiting the angle a to between about ten degrees and about ninety degrees (10°–90°) relative to a longitudinal axis L of the egg, the path of light passing through an egg and received by the spectrometer 16 does not pass through the aircell of the egg, except in the case of an inverted egg.

Figure 3B:
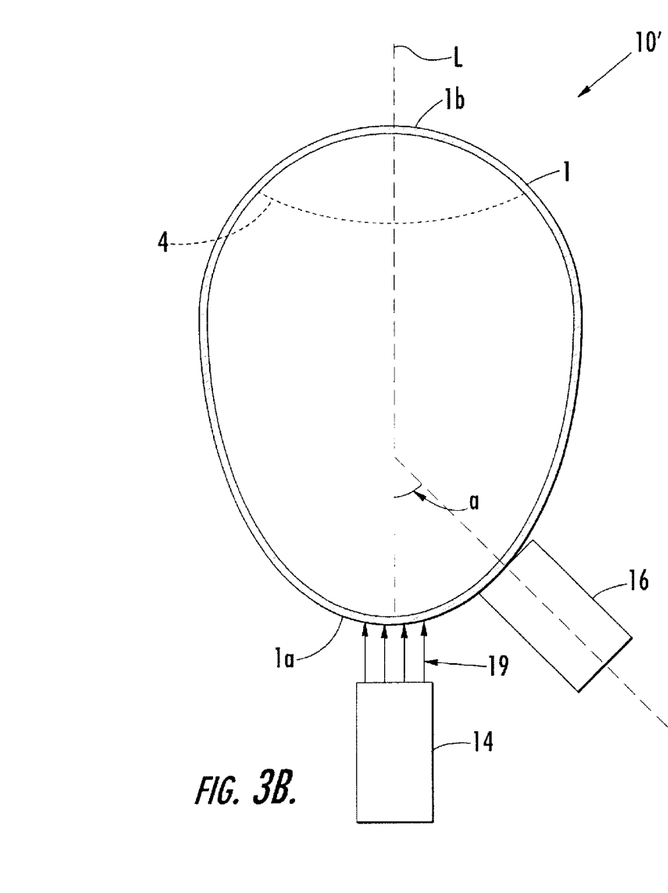

As illustrated in FIG. 3A, a light source 14 is preferably in adjacent, contacting relationship with egg 1 in order to reduce light reflected from the egg shell. According to an alternative embodiment of the present invention illustrated in FIG. 3B, an identifier 10' utilizes a light source 14 that emits a collimated light beam 19. By emitting a collimated light beam 19, the light source 14 need not be in contacting relationship with an egg in order to reduce light reflected from the egg shell. Similarly, the spectrometer 16 (or a detector portion of spectrometer 16) may be in contacting relationship with an egg, or may be spaced apart from an egg.

A light source 14 according to embodiments of the present invention may be a standard tungsten element candling device. Candling devices are well known to those of skill in the art, and need not be described further herein. An exemplary candling device that maybe used in accordance with embodiments of the present invention is a Reichert Model 650 available from Cambridge Instruments, Inc., Buffalo, N.Y.

Spectrometers are devices for measuring the intensity of radiation absorbed, reflected, or emitted by a material as a function of wavelength. Spectrometers are well known in the art and need not be described further herein. An exemplary spectrometer that may be utilized in accordance with embodiments of the present invention is an Ocean Optics S2000 spectrometer (Ocean Optics, Dunedin, Fla.).

Figure 4A:
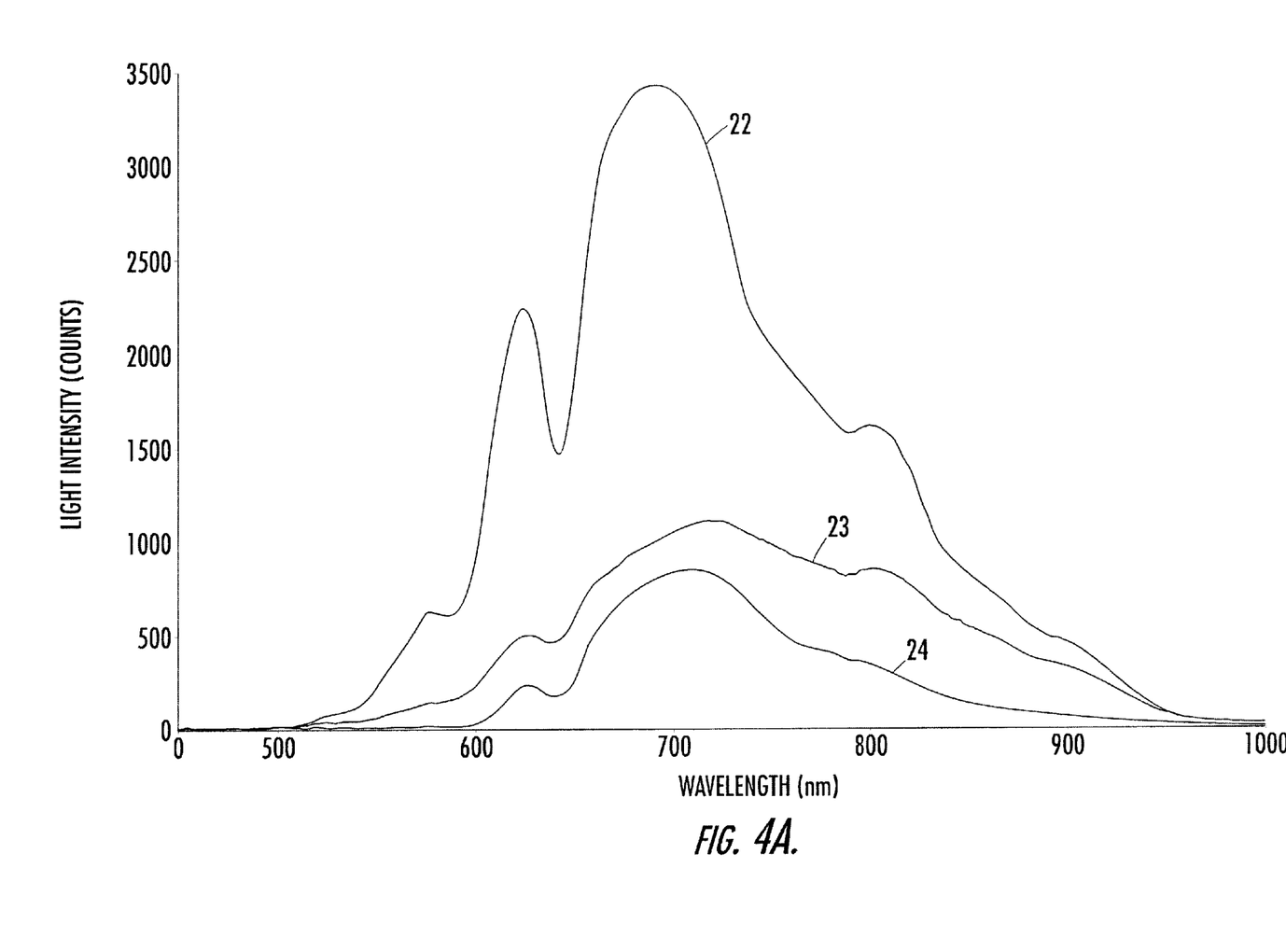
FIGS. 4A–4B illustrate exemplary spectra generated in accordance with embodiments of the present invention.
Figure 4B:
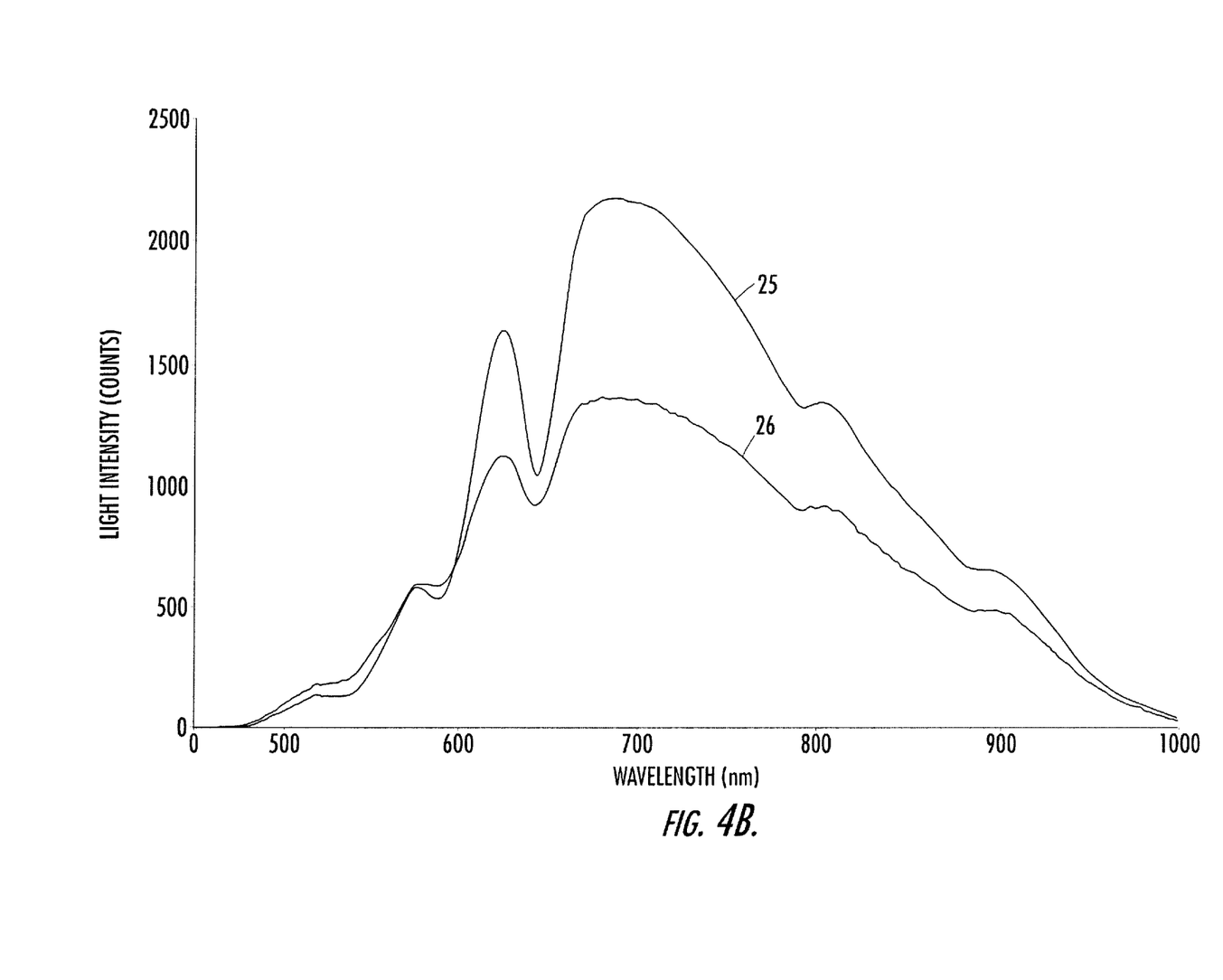

FIGS. 4A–4B illustrate exemplary spectra generated in accordance with embodiments of the present invention. FIG. 4A illustrates three spectra for three respective eggs. Wavelength in nanometers (nm) is plotted along the X axis, and light intensity counts are plotted along the Y axis. Spectrum 22 is associated with a clear egg. Spectrum 23 is associated with an early dead egg. Spectrum 24 is associated with a live egg. FIG. 4B illustrates two spectra 25, 26 for two respective rotted eggs. Wavelength in nanometers (nm) is plotted along the X axis, and light intensity counts are plotted along the Y axis. As illustrated, the spectra 25, 26 of the two rotted eggs are similar.

Figure 5:
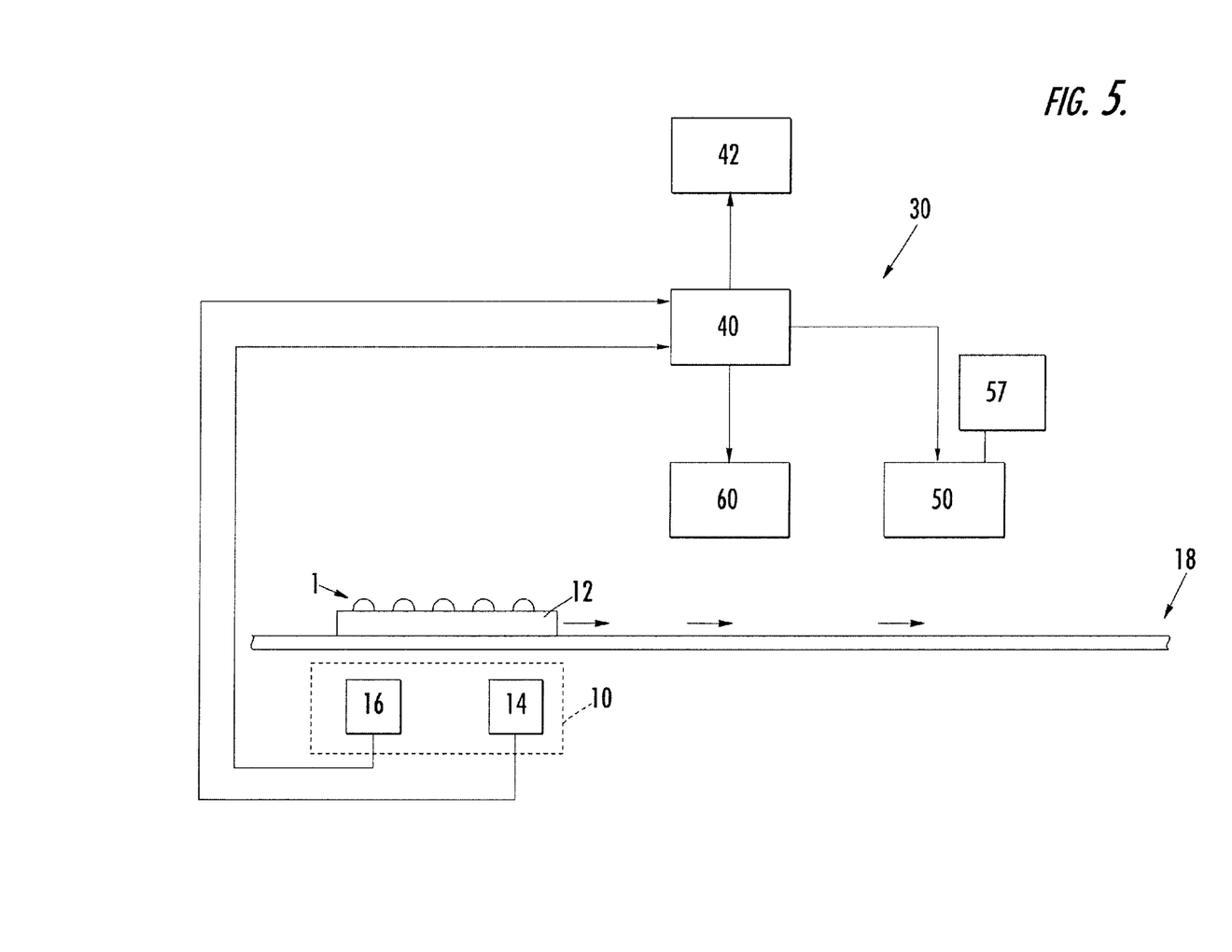
FIG. 5 is a block diagram of a system for processing eggs that includes an identifier for use in non-invasively identifying a present condition of an egg, according to embodiments of the present invention.

Referring now to FIG. 5, an apparatus 30 for processing eggs, according to embodiments of the present invention, is illustrated. An identifier 10, including a light source 14 and spectrometer 16 is operatively connected to a controller 40. The controller 40 controls the light source 14 and receives and processes signals from the spectrometer 16. The controller 40 also compares a spectrum generated for an egg with a plurality of spectra associated with known egg conditions and, using this comparison data, classifies an egg according to type (i.e., fertile, live, clear, dead, rotted, cracked, inverted, containing a substance to be harvested). An operator interface (e.g., a display) 42 is preferably provided to allow an operator to interact with the controller 40.

A sorting station 60 may be provided downstream of the identifier 10. The controller 40 generates a selective removal signal based on the presence and relative position of each suitable egg to cause the sorting station 60 to remove eggs having various identified conditions (e.g., eggs identified as being live, dead, clear, rotted, cracked, and/or inverted).

In the illustrated embodiment, a treatment station 50 is provided downstream of the identifier 10. The controller 40 generates a selective treatment signal based on the presence and relative position of each suitable egg to cause the treatment station 50 to treat, for example, by inoculation with a treatment substance, eggs having certain identified conditions (e.g., live eggs). The treatment station 50 may include at least one reservoir 57 for holding a treatment substance to be injected into eggs identified as suitable.

Treatment station 50 may also be configured to remove material from certain eggs upon receiving a respective signal from the controller 40. For example, substances to be harvested from eggs including, but not limited to, vaccines and recombinant protein products, may be removed from certain eggs upon receiving a respective signal from the controller 40.

A conveying system 18 serves to transport a flat 12 of eggs 1 through and, optionally, between, the identifier 10 and the sorting and treating stations 50, 60. Egg conveying systems are well known to those of skill in the art and need not be described further herein.

Although eggs conventionally are carried in egg flats, any means of presenting a plurality of eggs over time to the identifier 10 for identifying the present condition of eggs can be used. Moreover, eggs may pass one at a time through the identifier 10 or, the identifier 10 may be configured so that a number of eggs (i.e., within a flat) can pass through the identifier 10 simultaneously.

Egg flats of virtually any type may be used in accordance with embodiments of the present invention. Flats may contain any number of rows, such as seven rows of eggs, with rows of six and seven being most common. Moreover, eggs in adjacent rows may be parallel to one another, as in a "rectangular" flat, or may be in a staggered relationship, as in an "offset" flat. Examples of suitable commercial flats include, but are not limited to, the "CHICKMASTER 54"

flat, the "JAMESWAY 42" flat and the "JAMESWAY 84" flat (in each case, the number indicates the number of eggs carried by the flat). Egg flats are well known to those of skill in the art and need not be described further herein.

The controller 40 preferably is configured to: 1) generate control signals to actuate and deactuate one or more light sources 14; 2) receive and process signals from the spectrometer 16; 3) process and store data associated with each egg; and 4) generate control signals to operate the treatment station 50 and the sorting station 60.

The controller 40 preferably includes a processor or other suitable programmable or non-programmable circuitry including suitable software. The controller 40 may also include such other devices as appropriate to control the one or more light sources 14 and spectrometer 16, process or otherwise assess and evaluate signals from the spectrometer 16. Suitable devices, circuitry and software for implementing a controller 40 will be readily apparent to those of ordinary skill in the art upon reading the foregoing and following descriptions and the disclosures of U.S. Pat. No. 5,745,228 to Hebrank et al. and U.S. Pat. No. 4,955,728 to Hebrank.

The operator interface 42 may be any suitable user interface device and preferably includes a touch screen or keyboard. The operator interface 42 may allow the user to retrieve various information from the controller 40, to set various parameters and/or to program/reprogram the controller 40. The operator interface 42 may include other peripheral devices, for example, a printer and a connection to a computer network.

The identified conditions of each of a plurality of eggs in a flat can be displayed graphically via the operator interface 42 along with cumulative statistics for a group or flock of eggs. Such cumulative statistics may be assembled, calculated and/or estimated by the controller 40 using the classification data. The cumulative statistics may include, for each group, flock or flat, fertility percentage, early dead percentage, middead percentage, upside-down percentage and percentage of rots. These statistics may be useful to monitor and evaluate hatchery and incubator operation, and status and performance of breeds or flocks.

A flat 12 of classified eggs 1 is then placed on the conveyor 18 which transports the flat through the sorting station 60. The sorting station 60 physically removes the clear and early dead eggs from the flat 18 and directs them to a collector. The clear and early dead eggs may be used for purposes other than hatching broilers. For example, the clear and early dead eggs may be used in the production of shampoo and dog food and are more desirable when not contaminated with rotted eggs. The sorting station 60 may also remove the empty, rotted, mid-dead and late dead eggs and direct them to a separate collector. Alternatively, the sorting station 60 may be configured to remove live eggs.

The sorting station 60 may employ suction-type lifting devices as disclosed in U.S. Pat. No. 4,681,063 or in U.S. Pat. No. 5,017,003 to Keromnes et al., the disclosures of which are hereby incorporated by reference in their entireties. Any other suitable means for removing the eggs may be used as well, such apparatus being known to those of ordinary skill in the art.

The sorting station 60 preferably operates automatically and robotically. Alternatively, selected eggs may be identified on the operator interface 42, optionally marked, and removed by hand. The sorting station 60 may be provided downstream of the treatment station 50, in which case the non-live eggs will pass through the treatment station but will not be inoculated.

Following the sorting station 60, the flat 18 is conveyed through the treatment station 50. The flat may at this time hold all of the eggs which have not been removed, for example those eggs classified as live eggs. The treatment station 50 may treat the remaining eggs in any desired, suitable manner. It is particularly contemplated that the treatment station 50 may inject the remaining, "live" eggs with a treatment substance, and/or remove material therefrom.

As used herein, the term "treatment substance" refers to a substance that is injected into an egg to achieve a desired result. Treatment substances include but are not limited to vaccines, antibiotics, vitamins, virus, and immunomodulatory substances. Vaccines designed for in ovo use to combat outbreaks of avian diseases in hatched birds are commercially available. Typically, the treatment substance is dispersed in a fluid medium, (e.g., is a fluid or emulsion) or is a solid dissolved in a fluid, or a particulate dispersed or suspended in a fluid.

As the flat 18 of eggs 5 is conveyed through the treatment station 50, the controller 40 selectively generates an injection signal to the treatment station 50 to inject those eggs which have been classified by the controller 40 as live eggs or eggs otherwise suitable for injection. As used herein, the "selective generation of an injection signal" (or the generation of a selective injection signal), refers to the generation by the controller of a signal that causes injection only of those eggs identified by the identifier 10 as suitable for injection. As will be apparent to those skilled in the art, generation of a selective injection signal may be achieved by various approaches, including generating a signal that causes the injection of suitable eggs, or generating a signal that prevents the injection of non-suitable eggs.

A preferred treatment station 50 for use in accordance with embodiments of the present invention is the INOVOJECT® automated injection system (Embrex, Inc., Research Triangle Park, N.C.). However, any in ovo injection device capable of being operably connected, as described herein, to the controller 40 is suitable for use according to embodiments of the present invention. Suitable injection devices preferably are designed to operate in conjunction with commercial egg carrier devices or flats, examples of which are described herein above.

Methods and apparatus for non-invasively identifying egg conditions according to the present invention may be combined with methods and apparatus for classifying eggs that utilize opacity and temperature measurements of eggs as described in co-assigned and co-pending U.S. patent application Ser. No. 09/563,218, which is incorporated herein by reference in its entirety.

Experimental Results 1

Four hundred and fifty (450) eggs obtained from a commercial hatchery were illuminated with light from a standard tungsten bulb candler source in both visible and invisible wavelengths in a range of between about three hundred fifty nanometers and about one thousand nanometers (350 nm–1, 000 nm). A spectrum was obtained via an Ocean Optics S2000 spectrometer for each egg as described above, wherein each spectrum represented light intensity at selected ones of the visible and infrared wavelengths for a respective egg. (Sample spectra are illustrated in FIGS. 4A–4B, which were described above.) Data acquisition was performed using OOIBase32 in an Ocean Optics software package which interfaced a personal computer to the S2000 spectrometer and transferred acquired spectra from the S2000 spectrometer to the computer. Data analysis was performed with Galactic Industries Corporation Grams/32 v.5 with PLSplus/IQ. PLSplus/IQ is a chemometrics analysis add-on for GRAMS/32. Chemometrics is the process of using linear algebra to make quantitative or qualitative analyses of spectra. After generating a spectrum for each egg, the eggs were necropsied to determine the actual condition and age of the embryo in each egg.

It was discovered that the overall intensity counts of the signal (representing light passing through an egg) dropped significantly along the following progression: clear (infertile) egg, early dead egg, middle dead egg, late dead egg, live egg. The range of signal intensity over this progression (from clear to live) was about three (3) orders of magnitude (i.e., about one thousand times (1,000×)).

There were three (3) main peaks in the spectra for each egg, located at about six hundred thirty nanometers (630 nm), seven hundred nanometers (700 nm), and eight hundred nanometers (800 nm). These peaks were found to become shifted to higher values as embryo age increased.

At least two (2) rotted eggs were in the set and each produced a distinct spectrum compared to the other conditions (dead, live, clear, cracked, and inverted). The amplitude of the respective signal for each of the rotted eggs was comparable to a middle dead egg, but there were two to three (2–3) additional peaks present at about five hundred thirty nanometers (530 nm), five hundred seventy nanometers (570 nm), and nine hundred nanometers (900 nm).

In addition, eggs that were cracked and dried or inverted each produced a distinct spectrum compared to the other conditions. Cracked and dried eggs were found to have spectra that saturate the detector, resulting in a flat spectrum across most of the bandwidth (i.e., 350 nm–1,000 nm). Inverted eggs produced a spectrum that was distorted and that looked somewhat like an early dead egg.

Experimental Results 2

Figure 6:
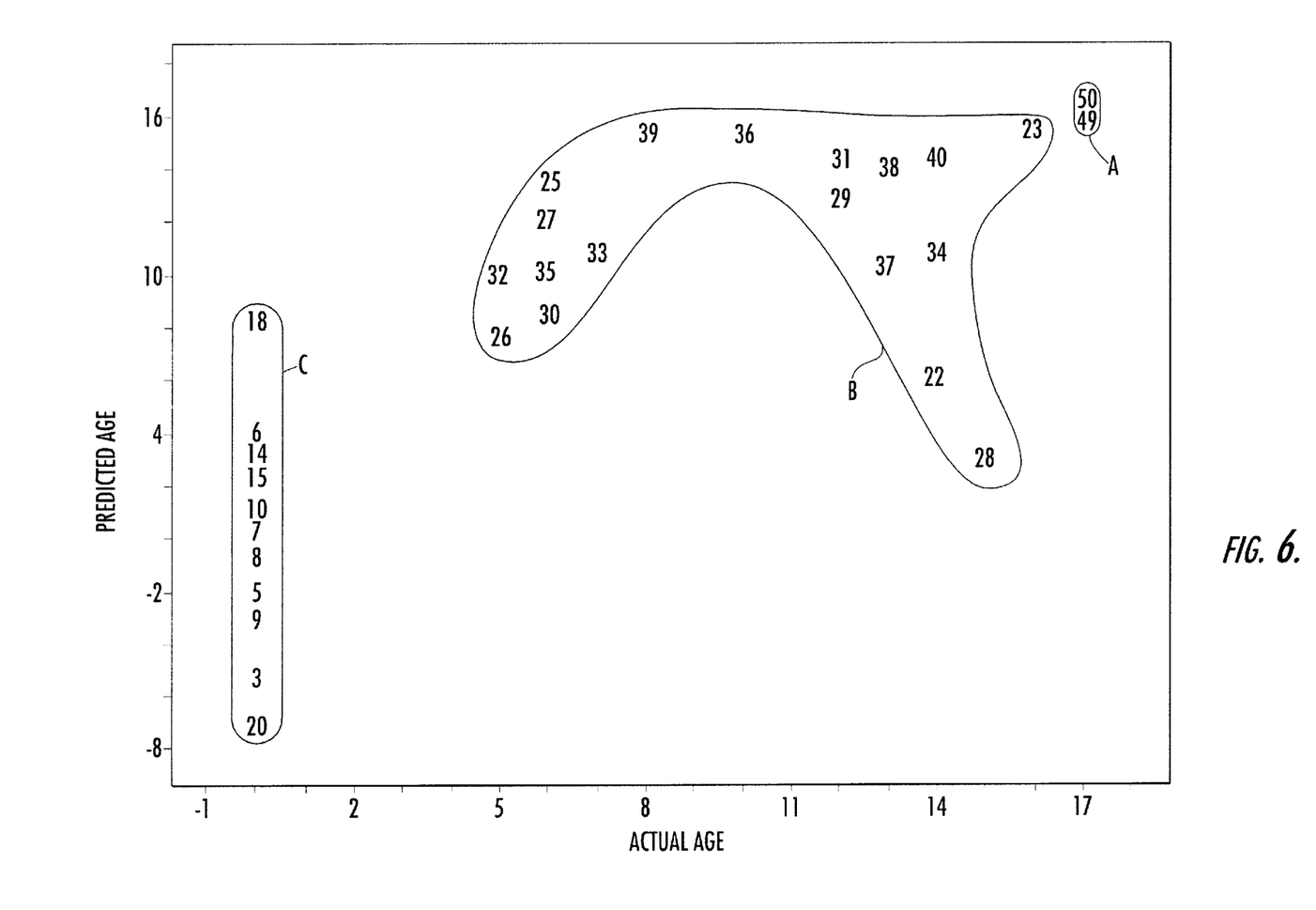
FIG. 6 is a graph that illustrates results of a model for predicting the present condition of eggs, according to embodiments of the present invention.

A mathematical model PLS-1 (Partial Least Squares) was developed using sixty (60) acquired spectra from 20 live eggs, 20 dead eggs, and 20 clear eggs. The model was designed to solve for a variable called "age", based upon necropsy results and produced the clusters illustrated in FIG. 6. The X axis represents actual age of an embryo based on necropsy results. The Y axis represents predicted age from spectra in accordance with methodology of the present invention. As illustrated in FIG. 6, all 20 live eggs were accurately predicted and appear stacked on top of each other at area A. Area B illustrates the predicted age of the 20 dead eggs which follow a clear, non-linear pattern. Area C illustrates the predicted age of the 20 clear eggs.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A method of non-invasively identifying a present condition of an egg, comprising:
    illuminating the egg with light from a light source, wherein the light includes light in both visible and infrared wavelengths;
    receiving light passing through the egg at a detector positioned adjacent the egg;
    determining intensity of the received light at a plurality of the visible and infrared wavelengths;
    generating a spectrum that represents light intensity at selected ones of the plurality of visible and infrared wavelengths; and
    comparing the generated spectrum with at least one spectrum associated with a known egg condition to identify a present condition of the egg.

2. The method according to claim 1, wherein the step of illuminating the egg with light comprises illuminating the egg with light at wavelengths of between about three hundred nanometers and about eleven hundred nanometers (300 nm–1,100 nm).

3. The method according to claim 1, wherein the light source is positioned adjacent a pointed end of the egg, and wherein the detector is positioned adjacent the light source.

4. The method according to claim 1, wherein the light source is positioned adjacent a pointed end of the egg, wherein the detector is positioned adjacent the egg at an angle of between about ten degrees and about ninety degrees (10°–90°) relative to a longitudinal axis of the egg, and wherein the pointed end of the egg defines zero degrees (0°) relative to the longitudinal axis.

5. The method according to claim 1, wherein the step of comparing the generated spectrum with at least one spectrum associated with a known egg condition comprises comparing the generated spectrum with a plurality of spectra associated with a respective plurality of known egg conditions.

6. The method according to claim 5, wherein the plurality of known egg conditions are selected from the group consisting of fertile eggs, live eggs, early dead eggs, middle dead eggs, late dead eggs, clear eggs, cracked eggs, rotted eggs, inverted eggs, and eggs containing an identified substance.

7. The method according to claim 6, further comprising the step of injecting a substance into the egg upon determining that the egg is a live egg.

8. The method according to claim 6, further comprising the step of removing material from the egg upon determining that the egg is a live egg.

9. The method according to claim 6, further comprising the step of removing the egg upon determining that the egg is a clear or early dead egg.

10. A method of non-invasively identifying a present condition of each of a plurality of eggs, comprising:
    illuminating each egg with light from a light source, wherein the light includes light in both visible and infrared wavelengths;
    receiving light passing through each egg at a detector positioned adjacent each egg;
    determining intensity of the received light at selected ones of the visible and infrared wavelengths for each egg;
    generating a spectrum for each egg that represents light intensity at the plurality of visible and infrared wavelengths;
    comparing the generated spectrum for each egg with a spectrum associated with a live egg to identify live eggs; and injecting a substance into eggs identified as live.

11. The method according to claim 10, further comprising:
comparing the generated spectrum for each egg with a spectrum associated with a dead egg to identify dead eggs; and
removing eggs identified as dead.

12. The method according to claim 11, further comprising the step of using removed eggs in processing one or more products.

13. The method according to claim 10, further comprising:
comparing the generated spectrum for each egg with a spectrum associated with a live egg to identify live eggs; and
removing eggs identified as live.

14. The method according to claim 10, further comprising:
comparing the generated spectrum for each egg with a spectrum associated with a clear egg to identify clear eggs; and
removing eggs identified as clear.

15. The method according to claim 14, further comprising the step of using removed eggs in processing one or more products.

16. The method according to claim 10, further comprising:
comparing the generated spectrum for each egg with a spectrum associated with a cracked egg to identify cracked eggs; and
removing eggs identified as cracked.

17. The method according to claim 10, further comprising:
comparing the generated spectrum for each egg with a spectrum associated with a rotted egg to identify rotted eggs; and
removing eggs identified as rotted.

18. The method according to claim 10, further comprising:
comparing the generated spectrum for each egg with a spectrum associated with an inverted egg to identify inverted eggs; and
removing eggs identified as inverted.

19. The method according to claim 10, wherein the step of illuminating each egg with light comprises illuminating each egg with light at wavelengths of between about three hundred nanometers and about eleven hundred nanometers (300 nm–1,100 nm).

20. The method according to claim 10, wherein a light source is positioned adjacent a pointed end of each egg, and wherein a detector is positioned adjacent each light source.

21. The method according to claim 10, wherein a light source is positioned adjacent a pointed end of each egg, wherein a detector is positioned adjacent each egg at an angle of between about ten degrees and about ninety degrees (10°–90°) relative to a longitudinal axis of the egg, and wherein the pointed end of the egg defines zero degrees (0°) relative to the longitudinal axis.

22. The method according to claim 10, further comprising the step of removing material from eggs identified as live.

23. An apparatus for non-invasively identifying a present condition of an egg, comprising:
a light source that illuminates an egg with light in both visible and infrared wavelengths;
a spectrometer that receives light passing through the egg, wherein the spectrometer obtains intensity values of the received light at selected ones of the visible and infrared wavelengths, converts light intensity values into a spectrum, and compares the spectrum with at least one spectrum associated with a known egg condition to identify a present condition of the egg.

24. The apparatus according to claim 23, wherein the light source illuminates an egg with light at wavelengths of between about three hundred nanometers and about eleven hundred nanometers (300 nm–1,100 nm).

25. The apparatus according to claim 23, wherein the light source is configured to be positioned adjacent a pointed end of the egg, and wherein the spectrometer is configured to be positioned adjacent the light source.

26. The apparatus according to claim 23, wherein the light source is configured to be positioned adjacent a pointed end of the egg, wherein the spectrometer is configured to be positioned adjacent the egg at an angle of between about ten degrees and about ninety degrees (10°–90°) relative to a longitudinal axis of the egg, and wherein the pointed end of the egg defines zero degrees (0°) relative to the longitudinal axis.

27. The apparatus according to claim 23, wherein the light source comprises a tungsten element.

28. The apparatus according to claim 23, wherein the spectrometer is configured to compare the generated spectrum with a plurality of spectra associated with a respective plurality of known egg conditions, and wherein the plurality of known egg conditions are selected from the group consisting of fertile eggs, live eggs, early dead eggs, middle dead eggs, late dead eggs, clear eggs, cracked eggs, rotted eggs, inverted eggs, and eggs containing an identified substance.

29. An apparatus for processing eggs, comprising:
an identifier configured to determine a present condition of a plurality of eggs, the identifier comprising:
a light source that illuminates each egg with light in both visible and infrared wavelengths;
a spectrometer that receives light passing through each egg, wherein the spectrometer obtains intensity values of the received light at selected ones of the visible and infrared wavelengths, converts light intensity values for each egg into a respective spectrum, and compares each generated spectrum with a plurality of spectra associated with a respective plurality of known egg conditions, wherein the plurality of known egg conditions are selected from the group consisting of fertile eggs, live eggs, dead eggs, clear eggs, cracked eggs, rotted eggs, inverted eggs, and eggs containing an identified substance; and
a display that displays the identified present condition of the eggs.

30. The apparatus according to claim 29, further comprising an egg removal apparatus configured to remove eggs identified as fertile, live, dead, clear, cracked, rotted, inverted, or containing an identified substance.

31. The apparatus according to claim 29, further comprising a plurality of injectors, wherein each injector is configured to inject a substance into a respective egg identified as a live egg.

32. The apparatus according to claim 29, further comprising a plurality of injectors, wherein each injector is configured to remove material from a respective egg identified as a live egg.

33. The apparatus according to claim 29, wherein the light source illuminates each egg with light at wavelengths of between about three hundred nanometers and about eleven hundred nanometers (300 nm–1,100 nm).

34. The apparatus according to claim 29, wherein the light source is configured to be positioned adjacent a pointed end of each egg, and wherein the spectrometer is configured to be positioned adjacent the light source.

35. The apparatus according to claim 29, wherein the light source is configured to be positioned adjacent a pointed end of each egg, wherein the spectrometer is configured to be positioned adjacent each egg at an angle of between about ten degrees and about ninety degrees (10°–90°) relative to a longitudinal axis of each egg, and wherein the pointed end of each egg defines zero degrees (0°) relative to the longitudinal axis.

36. The apparatus according to claim 29, wherein the light source comprises a tungsten element.

* * * * *